United States Patent [19]

Andrews

[11] 4,230,880
[45] Oct. 28, 1980

[54] 2,5-DIKETOGLUCONIC ACID ESTERS

[75] Inventor: Glenn C. Andrews, Waterford, Conn.

[73] Assignee: Pfizer Inc., New York, N.Y.

[21] Appl. No.: 12,683

[22] Filed: Feb. 16, 1979

Related U.S. Application Data

[60] Division of Ser. No. 843,946, Oct. 20, 1977, Pat. No. 4,159,990, which is a continuation-in-part of Ser. No. 749,509, Dec. 10, 1976, abandoned.

[51] Int. Cl.$^3$ ............................................. C07C 69/675
[52] U.S. Cl. ................................................... 560/174
[58] Field of Search ........................................ 560/174

[56] References Cited

U.S. PATENT DOCUMENTS 3,654,316  4/1972  Oga et al. .......................... 260/345.7

OTHER PUBLICATIONS

Wakisaka, Agr. Biol. Chem., 28, 819 (1964).
Katznelson, J. Biol. Chem., 204, 43 (1953).
Bernaerts et al., Antonie van Leeuwenhoeck, 37, 185 (1971).
Wagner et al., Synthetic Organic Chemistry, John Wiley & Sons, Inc., N. Y., pp. 261, 262, 480–481, 1965.

*Primary Examiner*—G. T. Breitenstein
*Attorney, Agent, or Firm*—Francis X. Murphy; Charles J. Knuth; Peter C. Richardson

[57] ABSTRACT

The novel stereoselective and regioselective alkali metal borohydride reduction of 2,5-diketogluconic acid, alkyl esters or salts thereof to form 2-ketogluconic acid together with lesser amounts of 2-ketogluconic acid is disclosed. The 2-ketogluconic acid is readily converted to ascorbic acid.

3 Claims, No Drawings

2,5-DIKETOGLUCONIC ACID ESTERS

CROSS REFERENCE TO RELATED APPLICATION

This application is a division of copending U.S. Pat. application Ser. No. 843,946, filed on Oct. 20, 1977, now U.S. Pat. No. 4,159,990, which is a continuation-in-part of U.S. application Ser. No. 749,509, filed on Dec. 10, 1976, abandoned.

BACKGROUND OF THE INVENTION

This invention relates to a process for preparing a mixture of 2-ketogulonic and 2-ketolgluconic acid or salts of these acids by the selective reduction of 2,5-diketogluconic acid, alkyl esters or salts thereof. The mixture of 2-ketogulonic acid and 2-ketogluconic acid is useful for the preparation of ascorbic and erythorbic acids. Ascorbic acid, or Vitamin C, is required in the human diet and is widely employed in both tablet form and as an additive in other foodstuffs to meet this need. Erythorbic acid, or isoascorbic acid, is useful as an antioxidant for use in foodstuffs.

2,5-diketogluconic acid is readily prepared by bacterial action on glucose, several species of Acetobacter and Pseudomonas being useful for this purpose. Japanese Patent No. 14493 (1964) to Shionogi and Co., Ltd. describes the use of *Pseudomonas sesami* for this preparation.

Prior work relating to the sodium borohydride reduction of 2,5-diketogluconic acid has been confined to complete reduction of both the 2-keto and 5-keto groups to hydroxy, using a large excess of sodium borohydride and the preparation of 2-ketogulonic acid and 2-ketogluconic acid by stereoselective and regioselective non-catalytic reduction is not known to have been reported. Wakisaka, Agr. Biol. Chem. 28, 819 (1964), reduced 2,5-diketogluconic acid at both the 2- and 5-keto positions by the action of excess sodium borohydride. The four isomers obtained were indicated to be D-gluconic acid, D-mannoic acid, L-idonic acid and L-gulonic acid. Ruffs oxidation of the resulting mixture of these isomers gave D-arabinose and L-xylose. The yield of D-arabinose obtained was greater than that of L-xylose which Wakisaka suggested might arise by either stereospecific reduction, by the presence of impurities or by transformations between the various structural isomers. The greater yield of D-arabinose suggests that reduction of hydride to form the D-isomers was greater than that to form the L-isomers, in contrast to the present process, which affords not only regioselective reduction at the 5-keto position but stereoselective reduction to form greater amounts of the desired L-isomers of 2-ketogulonic acid. Complete reduction of 2,5-diketogluconic acid with an excess of sodium borohydride was also reported by Katznelson, J. Biol. Chem., 204, 43 (1953), who obtained a "gluconic acid", considered to probably consist of four isomers which could not be resolved in his experiments. Similarly, the complete reduction of calcium 2,5-diketogluconate with sodium borohydride has been reported by Bernaerts et al, Antonie van Leeuwenhoeck, 37, 185 (1971).

Catalytic reduction of 2,5-diketogluconic acid using a Raney Nickel catalyst and hydrogen has been shown by Wakisaka, Agr. Biol. Chem. 28, 819 (1964), to give low yields of a mixture of 2-ketogulonic acid and 2-ketogluconic acid with 2-ketogluconic acid being the major product. This is undesirable if it is sought to utilize the mixture to prepare and isolate the more valuable ascorbic acid in high yields. For such purposes a mixture containing a major proportion of 2-ketogulonic acid is desirable, since 2-ketogulonic acid is the precursor of ascorbic acid while 2-ketogluconic acid is the precursor of erythorbic acid.

The catalytic reduction of a 5-keto-D-gluconate using noble metal catalysts to produce a mixture of an L-idonate and a D-gluconate is also known. Selectivity to the L-idonate is enhanced by use of a metal boride catalyst prepared by treating a noble metal salt with sodium borohydride, Chen et al Chem. Pharm. Bull., 18, 1305 (1970). The sodium borohydride reduction of 5-keto-D-gluconic acid has also been described, J.A.C.S., 76, 3543 (1954), but is non-stereoselective, affording approximately equal amounts of D-gluconic acid and L-idonic acid.

SUMMARY OF THE INVENTION

This invention relates to a process for preparing a mixture of a 2-ketogulonate and a 2-ketogluconate which comprises selectively reducing a 2,5-diketogluconate selected from 2,5-diketogluconic acid, a normal alkyl ester of 2,5-diketogluconic acid wherein said alkyl group is of 1 to 4 carbon atoms, and a salt of 2,5-diketogluconic acid having a counterion selected from an alkali metal, an alkaline earth metal, ammonium and tetra-alkyl ammonium, wherein the alkyl groups have from 1 to 4 carbon atoms. The selective reduction is effected by contacting the 2,5-diketogluconate in solution at a pH greater than 5 with between about 0.8 and 1.1 equivalents of an alkali metal borohydride per mole of 2,5-diketogluconate at a temperature of $-30°$ C. to $50°$ C. The resulting mixture of the 2-ketogulonate and 2-ketogluconate can be converted to ascorbic and erythorbic acid. Also disclosed are novel alkyl esters of 2,5-diketogluconic acid and 5,5-dialkyl acetals thereof.

DETAILED DESCRIPTION OF THE INVENTION

The process of the present invention has unexpectedly been found to allow the regioselective and stereoselective non-catalytic reduction of a 2,5-diketogluconate at the 5-keto position in good overall yield to a mixture of a 2-ketogulonate and a 2-ketogluconate. The ratio of the products in the resulting mixture can be varied from about 85:15 to about 45:55 depending on the conditions and reagents utilized, as will be more fully described below. Of particular interest is that the present process can provide a good yield of a mixture containing predominantly 2-ketogulonic acid which can be converted in good yield to the more valuable ascorbic acid. However, mixtures containing approximately equal amounts of 2-ketogulonate and 2-ketogluconate are useful sources for the preparation of both ascorbic and erythorbic acids and the present process therefore offers advantages of flexibility for production of varying amounts of ascorbic and erythorbic acids.

The 2,5-diketogluconate used in the present invention may be either 2,5-diketogluconic acid or salts of the acid. Suitable salts include those having as counterions an alkali metal, an alkaline earth metal, ammonium and tetra-alkyl ammonium, where the alkyl groups have from 1 to 4 carbon atoms. Also useful as starting materials for the present process are the novel normalalkyl esters of 2,5-diketogluconic acid wherein the alkyl group is of 1 to 4 carbon atoms. As used in the specification and claims hereof, the terms 2,5-diketogluconate, 2-ketogulonate and 2-ketogluconate include the free acids and suitable alkyl esters and salts thereof as previously described. The 2,5-diketogluconic acid and salts thereof may be produced by any means known in the art. Generally, the 2,5-diketogluconate is produced as the calcium salt in aqueous solution by fermentation using methods well known in the fermentation industry, see for example Japanese Pat. No. 14493, and this may be used directly as the starting material for the present process. The 2,5-diketogluconate can also be produced by fermentation in the presence of other ions such as sodium and the resulting sodium 2,5-diketogluconate is likewise used directly as the starting material. In an alternative method, the 2,5-diketogluconate is prepared in the conventional way as the calcium 2,5-diketogluconate and converted to the desired compound by addition of a salt effective to precipitate calcium and leave the 2,5-diketogluconate in solution with the desired counterion. Thus, for example, sodium or ammonium 2,5-diketogluconate can be produced by addition of sodium or ammonium carbonate, respectively, to a solution of calcium 2,5-diketogluconate produced by fermentation. Calcium is precipitated as calcium carbonate leaving the 2,5-diketogluconate in solution with sodium or ammonium counterions. The free acids may also be neutralized with an appropriate hydroxide or other salt. If desired, the 2,5-diketogluconate can be isolated, purified and redissolved.

The normal alkyl esters of 2,5-diketogluconic acid wherein alkyl is of 1 to 4 carbon atoms are novel compounds useful as starting materials in the present process. The esters may be prepared by heating a solution of 2,5-diketogluconic acid or a suitable salt thereof in the appropriate normal alkanol of 50° C. to 100° C. in the presence of a catalytic amount of a strong acid, such as concentrated sulfuric acid, hydrochloric acid, p-toluene sulfonic acid and the like, to form the corresponding alkyl 2,5-diketogluconate-5,5-dialkyl acetal. Suitable salts of 2,5-diketogluconic acid include the alkali metal, alkaline earth metal, ammonium and tetra-alkyl ammonium salts, wherein each alkyl group of the tetra-alkyl ammonium ion has from 1 to 4 carbon atoms. The acetal is then hydrolyzed with aqueous acid at a temperature between about −10° C. and 80° C. to afford the desired alkyl ester of 2,5-diketogluconic acid. Suitable acids include aqueous hydrochloric acid, trifluoroacetic acid, sulfuric acid sulfonic acid ion-exchange resins and the like. The alkyl 2,5-diketogluconate-5,5-dialkyl acetal intermediates are also novel compounds. A preferred acetal and ester resulting from hydrolysis thereof are methyl 2,5-diketogluconate-5,5-dimethyl acetal and methyl 2,5-diketogluconate respectively.

When an alkali metal 2,5-diketogluconate is utilized as the starting material the sodium salt is preferred. The sodium salt has been found to be a particularly desirable starting material for making mixtures of a 2-ketogulonate and a 2-ketogluconate containing the 2-ketogulonate as the major product, thereby facilitating ascorbic acid synthesis. A preferred alkaline earth 2,5-diketogluconate is the calcium salt. When tetra-alkyl ammonium salts are employed, the tetra-methyl ammonium is preferred for reasons of cost and availability. A preferred alkyl ester starting material is methyl 2,5-diketogluconate.

A solution of the 2,5-diketogluconate is contacted with an alkali metal borohydride. Preferably, the reaction is effected in aqueous solution, optionally containing organic cosolvents such as, but not limited to, alkanols of 1 to 4 carbon atoms, alkanediols of 2 to 4 carbon atoms, acetonitrile, dimethyl sulfoxide and dimethyl formamide. Methanol is a preferred cosolvent. The concentration of the 2,5-diketogluconate is not critical but is preferably between 5 and 20 weight percent. The concentration of the 2,5-diketogluconate formed by fermentation is generally within this range and thereby provides a suitable aqueous solution of the starting material for use in the present process. When an alkyl ester is utilized as starting material the reaction may be conducted in anhydrous solvents such as alkanols, especially methanol, dimethyl sulfoxide and dimethyl formamide. In all cases, it is not necessary that the 2,5-diketogluconate be completely dissolved in the solvent, provided a substantial part of the starting material is in solution.

The alkali metal borohydride may be used in either solution or solid form. The preferred borohydride for use in the present process is sodium borohydride. It has been found that use of the sodium compound, particularly when used with the sodium 2,5-diketogluconate as substrate, leads to high ratios of 2-ketogulonate in the product mixture. The use of other alkali metal borohydrides has been found to give somewhat lower amounts of 2-ketogulonate and by choice of reagents mixtures having ratios of 2-ketogulonate:2-ketogluconate of 85:15 to 45:55 may be produced. This allows for some flexibility in utilization of these mixtures to give either ascorbic acid or erythorbic acid.

Good yields of a mixture of a 2-ketogulonate and a 2-ketogluconate may be obtained by employing between about 0.8 to 1.1 equivalents of the alkali metal borohydride per mole of 2,5-diketogluconate. By an equivalent of alkali metal borohydride is meant the stoichiometric amount necessary to convert the 5-keto group of the 2,5-diketogluconate to hydroxyl. This can also be expressed as 0.8 to 1.1 equivalents of hydride ion. One mole of alkali metal borohydride contains 4 equivalents of hydride ion and the amount of the reagent required can correspondingly be expressed as 0.200 to 0.275 moles of the alkali metal borohydride. It will be understood that the alkali metal borohydride in amounts less than about 0.8 equivalents per mole of 2,5-diketogluconate can be used to give selective reduction of the 2,5-diketogluconate. In this event, however, the yield of the mixture of 2-keto acids will be correspondingly lower. The present process is directed towards obtaining the optimum overall yields of the desired product mixture. It is intended that the specification and claims hereof include a method of practicing the present process wherein only a part of the 2,5-diketogluconate is reacted and unreacted starting material may be subsequently recycled for further reaction.

During the reaction of the 2,5-diketogluconate with the alkali metal borohydride, the pH of the solution should be maintained at greater than 5, preferably between 6 and 10.5. When 2,5-diketogluconic acid is employed as the starting material the pH should be adjusted to above 5 prior to the addition of the alkali metal borohydride. The pH of an aqueous solution of sodium or calcium 2,5-diketogluconate produced by fermentation is usually less than 5 and the pH should similarly be adjusted to a value greater than 5 prior to addition of the borohydride. This can be done by the addition of any base, but preferably a sodium compound such as sodium carbonate or sodium hydroxide is used. Alternatively, the pH may be adjusted simultaneously with the borohydride addition, by dissolving the borohydride in a basic solution, such as sodium hydroxide, such that on addition of the basic borohydride solution the pH of the aqueous solution is immediately adjusted to a value greater than 5. In this case, an allowance should be made for the small amount of borohydride that will be decomposed by the acidic conditions before the pH has been adjusted to greater than 5, by adding a small excess over the stoichiometric amount required.

The borohydride may be added slowly in portions over a period of time, for example by adding the basic solution of the borohydride dropwise while stirring the solution of the 2,5-diketogluconate. Preferably, the borohydride is added in one batch at the start of the reaction at a temperature below 25° C.

The reduction may also be effected in a flow reaction system, when generally a solution of the alkali metal borohydride is mixed with, or injected into, the 2,5-diketogluconate containing stream.

The time necessary to complete the reduction depends on the temperature of the reaction and the rate of addition of the borohydride to the 2,5-diketogluconate, but generally the reaction times will be relatively short and the reaction will be complete in times of about 10 minutes to about 2 hours.

During addition of the alkali metal borohydride, the temperature of the aqueous solution should be maintained at between about −30° C. to 50° C. and preferably −25° C. to 25° C. Above 50° C. decomposition of the reactants may be experienced.

Advantageously the reduction reaction may be conducted in the presence of a boron-complexing agent which is dissolved or dispersed in the reaction medium. Boric acid is produced in the reducible reaction and this may complex with the 2,5-diketogluconate starting material. By a boron-complexing agent is meant any compound or material that will inhibit or prevent the complexing of boric acid and the 2,5-diketogluconate, for example by preferentially reacting with or absorbing boric acid, but which is not deleterious to the reaction. Suitable boron-complexing agents include alkali metal fluorides, ammonium fluoride and boron-absorbing ion-exchange resins. A number of such resins are available commercially. A particularly useful example of the latter is Amberlite XE-243 (Rohm and Haas Company, Philadelphia, Pa.) Sufficient boron-complexing agent should be present to complex the boric acid produced. Thus, about four moles of fluoride should be used for every mole of sodium borohydride employed to effect the reduction. The amount of ion-exchange resin employed will usually be from about 0.5–1 volume of resin:1 volume of 2,5-diketogluconate solution in a batch process, but the amount used will of necessity vary according to the particular resin used and the reaction conditions.

On completion of the selective reduction to form the mixture of a 2-ketogulonate and a 2-ketogluconate, unreacted 2,5-diketogluconate can be recycled for further reaction, or it can be effectively removed by heating with acid or base. If it is desired to subject the unreacted 2,5-diketogluconate to further reduction reactions, the initial reduction is preferably conducted in the presence of a boron-complexing agent as described above herein.

The mixture of 2-ketogulonic and 2-ketogluconic acids can be isolated by filtering the reaction mixture and adjusting the filtrate to a pH between 1.5 and 2 by addition of acids such as concentrated sulfuric acid and filtering off and discarding any precipitate that is formed. The 2-ketogulonic and 2-ketogluconic acids can be collected by removing the water or water-organic co-solvent, for example, by freeze drying. The ratio of 2-ketogulonic acid to 2-ketogluconic acid in the mixture can be determined by liquid chromotography of the methyl esters using a mixture of boric acid (0.6 M) and ammonium formate (0.4 M) in water as a mobile phase with Aminex Resin Type A-25, (TM. BioRad Laboratories, Richmond, California), 50–100 mesh size as the stationary phase, or by thin layer chromatography using a cellulose support.

The mixture of 2-ketogulonic acid and 2-ketogluconic acid can readily be converted to ascorbic and erythorbic acids. The mixture of 2-keto acids can be converted to the methyl esters by refluxing in methanol in the presence of an acid catalyst such as hydrochloric acid or a sulfonic ion exchange resin for 3 to 24 hours. Other esters can be formed in this manner using the appropriate alcohol. The esters are formed directly when an alkyl ester of 2,5-diketogluconic acid is the starting material for the selective reduction. The mixture of methyl esters can be separated and is then refluxed in methanol in the presence of a base, such as sodium bicarbonate, in an inert atmosphere. On cooling, sodium ascorbate and sodium erthorbate precipitate out. The crude salts are collected by filtration, mixed with water and deionized with a cation exchange resin such as Dowex 50 manufactured by the Dow Chemical Co. The water is removed and the ascorbic acid and erythorbic acid are recrystallized from methanol-water to give a mixture of ascorbic and erythorbic acids. If desired, ascorbic acid may be obtained by recrystallization from a 4 to 1 methanol-water solution. Other suitable solvents or co-solvents can be used if desired. If desired, the methyl esters of 2-ketogulonic acid and 2-ketogluconic acid can be separated and converted to ascorbic acid and erythorbic acid respectively using the same conditions as described above for the mixture of esters.

In a preferred process, ascorbic acid can be prepared selectively from a mixture of 2-ketogulonic acid and 2-ketogluconic acid. This is particularly advantageous when the mixture containing a high proportion of 2-ketogulonic acid has been formed, as for example by the sodium borohydride reduction of sodium 2,5-diketogluconate. The mixture of acids obtained by the borohydride reduction is heated in a suitable organic solvent, such as xylene, to about 50° C. to 130° C., preferably 60° C. to 90° C. in the presence of an acid selected from hydrochloric acid, hydrobromic acid, sulfuric acid and sulfonic ion exchange resins. The preferred acid is hydrochloric acid. After heating for a period of 3 to 12 hours, depending on the temperature employed, lactonization of the 2-ketogulonic acid to ascorbic acid is substantially complete. In this process erythorbic acid is not produced and thereby affords a simple method of selectively forming ascorbic acid from mixtures of 2-ketogulonic acid and 2-ketogluconic acid produced by the borohydride reduction of a 2,5-diketogluconate. The acid catalyzed lactonization can also be used to convert mixtures of the alkyl esters of the 2-ketogulonic acid and 2-ketogluconic acid to ascorbic acid.

The present invention is illustrated by the following examples. It should be understood, however, that the invention is not limited to the specific details of these examples.

EXAMPLE 1

To a rapidly stirring solution of 20 l of filtered crude fermentation broth containing 10% calcium 2,5-diketogluconate ($C_6H_7O_7 \cdot 1.5H_2O$, mw 238, .84 M) at 0° (ice-water bath) was added 42.4 ml of 2.2 M $NaBH_4$ in 7 M NaOH (.93 M of H) at a rate of 1 ml/min. The pH of the solution increased rapidly from 3.65 to 10.2. The resulting slurry was filtered, the filtrate adjusted to pH 1.6 with concentrated $H_2SO_4$ and the resulting precipitate was removed by filtration and discarded. Removal of water by freeze drying afforded 246 g of freeze-dried solids. A portion of the above was esterified and analyzed by liquid chromatography with an internal standard to afford a 78:22 ratio of 2-ketogulonic acid:2-ketogluconic acid in an overall yield of 79%.

A solution of 10 g of freeze dried 2-ketogulonic and 2-ketogluconic acids from the above reduction in 50 ml MeOH was treated with 1 g Dowex 50 (T. M. Dow Chemical Co.) resin and refluxed for 12 hours. On cooling the resin was removed by filtration, and the crude methyl esters isolated removal of solvent as an oil.

The crude mixture of methyl esters from above was placed in methanol with 1.5 equivalents of $NaHCO_3$ and refluxed under a nitrogen atomosphere for 6 hours. On cooling, the sodium salts of ascorbic and erythorbic acids precipitated from solution. The crude salts were isolated by filtration, placed in water and de-ionized with Dowex 50 cation exchange resin. On removal of water the crude ascorbic erythorbic acid residue crystallized from methanol water to afford a mixture of ascorbic and erythorbic acids. Recrystallization from 4:1 methanol water afforded ascorbic acid.

EXAMPLE 2

A 10% aqueous solution of sodium 2,5-diketogluconate was adjusted to a pH of 6.1 by addition of sodium carbonate, methanol was added to give 50% by volume and the solution was cooled to between −15° C. and −25° C. One equivalent of sodium borohydride was added to the cooled solution which was stirred for six hours at −15° C. to −25° C. and at room temperature overnight. A mixture of sodium 2-ketogulonate and 2-ketogluconate was isolated by precipitation with methanol and filtration. Analysis of the methyl esters by liquid chromatography showed a 78:22 ratio of 2-ketogulonic acid to 2-ketogluconic acid in the product mixture.

EXAMPLE 3

Using the method of Example 2, sodium borohydride reduction of calcium 2,5-diketogluconate was conducted at 0° C. at different pH values. The mixtures of 2-ketogulonate and 2-ketogluconate formed were analyzed by liquid chromatography to determine the ratio of 2-ketogulonic acid to 2-ketogluconic acid. The results obtained were as follows:

| pH | Solvent | Ratio 2-ketogulonic acid: 2-ketogluconic acid |
|---|---|---|
| 6.37 | Water:Methanol (a) | 69:31 |
| 8.23 | Water:Methanol | 68:32 |
| 8.65 | Water | 45:55 |

(a) 1:1 by volume

EXAMPLE 4

Using the method of Example 2, sodium borohydride reduction of sodium 2,5-diketogluconate was conducted in water:methanol solution (1:1 by volume) maintained at between −15° C. and −20° C. at different pH values. The mixture of 2-ketogulonate and 2-ketogluconate formed were analyzed by liquid chromatography to determine the ratio of 2-ketogulonic acid to 2-ketogluconic acid. The results obtained were as follows:

| pH | Ratio of 2-ketogulonic acid: 2-ketogluconic acid |
|---|---|
| 6.10 | 78:22 |
| 8.60 | 77:23 |
| 8.80 | 77:23 |
| 10.20 | 71:29 |

EXAMPLE 5

Using the method of Example 2, sodium borohydride reduction of sodium 2,5-diketogluconate was conducted in water:methanol solution at pH between 7.9 and 8.6 at different temperatures. The ratios of 2-ketogulonic acid to 2-ketogluconic acid in the resulting products were determined by liquid chromotography. The results obtained were as follows:

| Temp °C. | Ratio of 2-ketogulonic acid: 2-ketogluconic acid |
|---|---|
| 24 | 77:23 |
| 0 | 80:20 |
| −15 to −20 | 77:23 |

EXAMPLE 6

Using the method of Example 2, sodium borohydride reduction of sodium 2,5-diketogluconic acid was conducted in water at 0° C. at a pH of 8 with varying concentrations of the sodium 2,5-diketogluconate. The ratios of the 2-ketogulonic acid to 2-ketogluconic acid in the resulting products were determined by liquid chromotography. The results obtained were as follows:

| Concentration of sodium 2,5-diketogluconate, wt. % | Ratio of 2-ketogulonic acid: 2-ketogluconic acid |
|---|---|
| 5 | 75:25 |
| 10 | 79:21 |
| 20 | 56:44 |

EXAMPLE 7

The reduction reaction was conducted using different alkali metal borohydride and 2,5-diketogluconates of different counter-ions. The ratios of 2-ketogulonic acid to 2-ketogluconic acid in the resulting mixtures were determined by liquid chromatography. The conditions of the reactions and the results obtained were as follows:

| Boro-hydride ion | 2,5-di-ketogluconate | Temp °C. | pH | Ratio of 2-keto-gulonic acid: 2-ketogluconic acid |
|---|---|---|---|---|
| Li | Li | −15 to −20 | 8.26 | 48:52 |
| Na | Li | −15 to −20 | 8.06 | 63:37 |
| Na | Na | −15 to −20 | 8.60 | 77:23 |
| Na | K | −15 to −20 | 8.08 | 64:36 |
| K | K | −15 to −20 | 7.97 | 67:33 |
| Na | Me4N | −15 to −20 | 8.61 | 63:37 |
| Na | Ca | 0° | 8.65 | 45:55 |
| Li | Li | 0 | 8.0 | 48:52 |
| Li | Na | 0 | 8.0 | 47:53 |
| Na | Li | 0 | 8.0 | 63:37 |
| Na | Na | 0 | 8.0 | 79:21 |

EXAMPLE 8

The reduction of calcium 2,5-diketogluconate ith 4.4 M sodium borohydride in 14 M sodium hydroxide was conducted at 0° C. in water containing various co-solvents. The ratios of the 2-ketogulonic acid to 2-ketogluconic acid in the resulting mixtures were determined by liquid chromotography. The results obtained were as follows:

| Co-solvent | Water: Co-solvent ratio | Ratio of 2-ketogulonic Acid: 2-ketogluconic acid |
|---|---|---|
| Ethylene glycol | 6:1 | 72:28 |
| Acetonitrile | 4:1 | 76:24 |
| Dimethyl formamide | 4:1 | 72:28 |
| Dimethyl sulfoxide | 6:1 | 71:29 |
| None | — | 77:23 |

EXAMPLE 9

15 g of isolated calcium 2,5-diketogluconate was dissolved in 150 ml of water and 6.61 g of sodium carbonate was added at 0° C. while stirring the solution. The pH of the solution increased to 9.57. 0.49 g of sodium borohydride was added to the solution at 0° C. After stirring for 15 minutes the mixture was filtered and the filtrate was passed over an acidic ion exchange resin. After freeze drying and formation of the methyl esters, as described in Example 1, analysis by liquid chromotography indicated a ratio of 2-ketogulonic acid to 2-ketogluconic acid of 85:15.

EXAMPLE 10

A suitable method of forming ascorbic acid is as follows: To a reaction flask is added 10 g of an 80:20 mixture of 2-ketogulonic acid and 2-ketogluconic acid. To this is added 15 ml of xylene and 2 ml of concentrated hydrochloric acid and the mixture is then heated to 65° for 5 hours during which time it is vigorously stirred. Ascorbic acid may be recovered from the reaction mixture and purified by recrystallization.

EXAMPLE 11

To 50 ml 20% sodium 2,5-diketogluconate at 0° C. was added 0.8 ml 10% sodium hydroxide to adjust the pH from 5.15 to 9.70. Sodium borohydride powder (11.26 mmole, Alfa Products, Danvers, Ma. 01923) was immediately added. With the pH at 10.60 after 10 minutes, the mixture was adjusted to a pH of 7 with concentrated sulfuric acid. Analysis of the reduced mixture by HPLC (Aminex A-25 resin using 0.5 M $NH_4^+HCO_2^-$ eluant) revealed clean reduction to a mixture of sodium 2-ketogulonate and sodium 2-ketogluconate in 85% yield.

To determine the ratio of 2-ketogulonate to 2-ketogluconate, the freeze-dried solution from 5 ml of the reduced mixture was esterified with 15 ml methanol and 0.275 ml concentrated sulfuric acid. The methyl ester obtained was analyzed by gas chromatography as its persilylated derivative (prepared by treatment with "Tri-Sil/TBT" [Pierce Chemical Company, Rockford, Ill. 61105]). Separation on a 3% OV-210 column at 135° C. (30 ml/min flow rate) showed an 85:15 ratio of methyl 2-ketogulonate acid to methyl 2-ketogluconate acid.

EXAMPLE 12

To a 1 liter, 3-necked round bottom flask equipped with nitrogen outlet, reflux condenser and mechanical stirrer was added 100 g (.042 mole) of calcium 2,5-diketogluconic acid tri-hydrate, 800 ml of methanol and 37 ml (0.84 mole) of concentrated sulfuric acid. The mixture was stirred at reflux overnight. On cooling to room temperature the mixture was filtered to remove precipitated calcium sulfate and passed down 500 ml of Amberlyst A-21 weakly basic ion-exchange resin (Rohm and Haas, Philadelphia, Pa.). On removal of solvent from the pale yellow filtrate, a crystalline compound precipitates from solution. After filtration, the residue was washed with cold methanol affording 24.6 g (23%) of methyl 2,5-diketogluconate-5,5-dimethyl acetal: mp 170°–172°; $[\alpha]_{23}{}^D = 37.97°$ (1 = 1 cm, H2O); mass spectrum m/e (70 eV) 203, 191, 175, 161, 157, 143, 133; ir (KBr) cm$^{-1}$ 1754 (C=O), 3333 (OH); nmr-(DMSO-d6) $\delta_H$ 6.55 (s, 1, OH), 4.64 (dblts, 2, —OH) 3.68 (s, 3,

3.33 and 3.22 (singlets, 6, (CH3O—)2C—); nmr (DMSO-d6) $\delta_c$ 170.71 (s, 1,

98.46 (s, 1, anomeric), 97.17 (s, 1, anomeric), 74.59 (d, 1, —C—OH), 72.60 (d, 1, —C—OH), 60.90 (t, 1, —CH2—O), 53.96 (q, 1, CH3O—), 49.73 (q, 1, CH3—O), 52.02 (q, 1, CH3—O—).

Anal. Calcd. for C9H16O8: C, 42.86; H, 6.39. Found: 43.13; H, 6.09.

EXAMPLE 13

To a 2 liter 3-necked round bottom flask equipped with nitrogen outlet, Soxhlet extractor, and mechanical stirring was added 28 g (112 mmole) of freeze dried sodium 2-5-diketogluconate, 1300 ml of methanol and 5 ml (90 mmole) of concentrated sulfuric acid. The mixture was refluxed for 11.5 hours. The methanol condensate was condensed and then passed through 20 g Linde molecular sieves #4A (Union Carbide Corp.) in a Soxhlet extraction thimble and returned to the reaction mixture. On cooling to room temperature the mixture was filtered to remove precipitated sodium sulfate and passed through 200 ml of Amberlyst A-21 weakly basic ion exchange resin (Rohm & Haas, Philadelphia, Pa. 19105). Treatment with decolorizing charcoal and subsequent filtration yielded a light orange filtrate which was concentrated in vacuo affording a white crystalline compound. The solid was collected and washed with cold methanol to afford 7.0 g (24%) of methyl 2,5-diketogluconate-5,5-dimethyl acetal identical in composition to that obtained from the calcium salt of 2,5-diketogluconic acid as shown in Example 12.

In certain instances, it has been found that the white crystalline precipitate consists of a mixture of the desired 5,5-dimethyl acetal and methyl comenate. NMR of methyl 2,5-diketogluconate-5,5-dimethyl acetal (DMSO-d$_6$): 3.68 (s, 3,

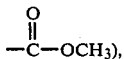

3.65 (s, 2, —CH$_2$—), 3.51 (d, 2,

J=2 Hz), 3.33 (s, 3, —OCH$_3$) and 3.22 (s, 3, —OCH$_3$)$_0$; methyl comenate (DMSO-d$_6$): S$_H$ 8.19 (s, 1, —H), 6.98 (s, 1, —H), and 3.86 (s, 3, —C—OCH$_3$). The presence of the methyl comenate can be eliminated by fractional elution through the Amberlyst A-21 column; the methyl comenate elutes last with methanol.

EXAMPLE 14

A 250 ml round-bottom flask charged with 5.0 g (19.8 mole) of methyl 2,5-diketogluconate-5,5-dimethyl acetal, 150 ml of water and 3 ml of 6 N hydrochloric acid was stirred at 80° for 45 min. cooled and the aqueous solution passed through a column containing 40 ml of Amberlyst A-21 ion exchange resin (Rohm and Haas Co., Philadelphia, Pa.). The neutralized eluent was then freeze-dried to afford 2.2 g (100%) of methyl 2,5-diketogluconate as a friable, unstable yellow powder, homogeneous by hplc analysis (Aminex A-25 resin using 0.5 M NH$_4$+HCO$_2$− eluent): Ir (KBr) cm$^{-1}$ 3330 (s, OH), 1736 (s, me-ester); nmr (D$_2$O) δ$_c$ 170.00 (s, ester carbon), 96.86 and 92.84 (singlets, anomeric), 73.20 and 71.50 (doublets, —CH—OH), 65.99 (t, —CH$_2$—O—), 53.95 (q, CH$_3$—O).

EXAMPLE 15

A 500 mg (1.98 mmole) sample of methyl 2.5-diketogluconate-5,5-dimethyl acetal, charged with 5 ml of 95:5 trifluoroacetic acid/H$_2$O, was stirred 5 minutes under nitrogen at room temperature. Trifluoroacetic acid/water was removed by evaporation in vacuo over 20 minutes. Methyl 2,5-diketogluconate was isolated as a white solid in 100% yield and was found to be homogeneous by HPLC analysis (Aminex A-25 resin using 0.5 M NH$_4$+HCO$_2$− eluant).

EXAMPLE 16

The product from Example 14 was placed in 150 ml of water, cooled to 0° and the pH adjusted to 7.5 with 1 N NaOH. To the rapidly stirring mixture was added 215 mg of sodium borohydride. After 1 minute, the mixture was run through 40 ml of an ion exchange column containing 50% Dowex 50 and 50% Amberlyst A-21 resin. The filtrate was concentrated in vacuo to a solid mixture of methyl 2-ketogulonate and methyl 2-ketogluconate comprising 3.7 gm. The crude solid was placed in 50 ml of 95% ethanol with 5.99 gm of sodium bicarbonate and refluxed for 4 hr under nitrogen. On cooling the reaction was deionized with excess Dowex 50 and then concentrated in vacuo to a yellow oil. Glpc analysis of the per-trimethylsilylated reaction mixture (150°, 5 ft OV-210 column) indicates a 78:22 ratio of ascorbic to erythorbic acids in a 20% overall yield by iodine titration.

EXAMPLE 17

To 50 ml of 12% aqueous sodium 2,5-diketogluconate (28.04 mmole) was added 45 ml Amberlite XE-243 ion exchange resin (Rohm & Haas, Philadelphia, Pa. 19105). The mixture was stirred to 0° C. in an ice water bath. With dropwise addition of 10% sodium hydroxide, the pH was adjusted to 10.8. Treatment with 0.265 g sodium borohydride (7.01 mmole, Alfa Products, Danvers, Ma. 01923) for 10 minutes was followed by adjustment to pH 7 with concentrated sulfuric acid. Stirring for 0.5 hour yielded upon filtration of the resin a reduced mixture from which ca. 50% of the boron initialy present was removed. A 90% yield of an 85.15 mixture of 2-ketogulonic and 2-ketogluconic acids was obtained.

EXAMPLE 18

To 50 ml of 12% aqueous sodium 2,5-diketogluconic acid (28.04 mmole) was added 35 ml Amberlite XE243 ion exchange resin (Rohm & Haas, Philadelphia, Pa. 19105). The mixture was stirred to 0° C. in an ice water bath. With dropwise addition of 10% sodium hydroxide, the pH was adjusted to 10.8. Upon addition of 0.212 g sodium borohydride (5.61 mmole, Alfa Products, Danvers, Ma. 01923) a pH rise to 11.55 was observed. After 10 minutes, the mixture was quenched with concentrated sulfuric acid to adjust the pH from 11.2 to 7. After stirring for 0.5 hour, the partially reduced mixture was filtered to remove the resin.

To the partially reduced solution was added an additional 10 ml Amberlite XE243 resin. After cooling back to 0° C., the solution was adjusted to pH 10.8 with 10% sodium hydroxide. An additional 53 mg (1.40 mmole) sodium borohydride was added. After 10 minutes, concentrated sulfuric acid was added to adjust the pH to 7. After stirring 0.25 hour, the mixture was filtered. HPLC analysis showed complete reduction of sodium 2,5-diketogluconate to sodium 2-ketogulonate and sodium 2-ketogluconate. Very little boric acid or the possible over-reduction products were observed. By using HPLC assay with 2-imidazolidone as internal standard, a 96% yield of an 85:15 mixture of 2-ketogulonic and 2-ketogluconic acids was determined.

EXAMPLE 19

To a rapidly stirring 12% aqueous solution of sodium 2,5-diketogluconate (28.04 mmole), cooled to 0° C. in an ice water bath, was added 2.355 g (56.08 mmole) sodium fluoride. With dropwise addition of 10% sodium hydroxide, the pH was adjusted from 4.3 to 10.8. Ten minutes after the addition of 0.530 g sodium borohydride (14.02 mmole, Alfa Products, Danvers, Ma. 01923), the pH was adjusted to 7 with concentrated sulfuric acid. HPLC analysis (Aminex A-25 resin using 0.5 M NH$_4$+HCO$_2$− eluant) revealed less boron present than without the sodium fluoride. Upon stirring the mixture overnight, a small amount of white solid precipitated and was removed by filtration. The yield of 85:15 mixture of 2-ketogulonic and 2-ketogluconic acids was determined to be 90%.

EXAMPLE 20

To a rapidly stirring solution of 55 mmole of sodium 2,5-diketogluconic acid in 150 ml of $H_2O$ at 0° and a pH of 9.5 was added 12.7 mmole of sodium borohydride over a period of 15 minutes. On completion of the addition, the pH of the solution was adjusted to approximately 7 with 6 N hydrochloric acid and freeze-dried to afford 16.3 g of solids. A 15.0 g portion of the freeze-dried solid was dissolved in 250 ml of methanol:-water/95:5 with 100 ml of Amberlyst 15 (Rohm and Haas, Philadelphia, pa. 19105) ion exchange resin and refluxed overnight. On cooling the resin was removed by filtration, the filtrate passed through 40 ml of Amberlyst A-21 (Rohm and Haas, Philadelphia, Pa. 19105) ion exchange resin and concentrated in vaccuo. Crystals which appeared on standing were removed by filtration and washed with acetone affording 2.21 g (21%) of methyl 2-ketogulonate (mp 150–154°, literature 155°–157°), shown by hplc analysis and $C_{13}$ spectroscopy to be 97% isomerically pure. The methyl 2-ketogulonate may be converted to ascorbic acid by heating with sodium bicarbonate under nitrogen.

What is claimed is:

1. A normal-alkyl ester of 2,5-diketogluconic acid wherein said alkyl group is of 1 to 4 carbon atoms.
2. An ester of claim 1 wherein said alkyl group is methyl, ethyl or n-propyl.
3. Methyl 2,5-diketogluconate.